United States Patent
Cekic et al.

(10) Patent No.: US 7,291,846 B2
(45) Date of Patent: *Nov. 6, 2007

(54) APPARATUS FOR AND METHOD OF TREATING A FLUID

(75) Inventors: Miodrag Cekic, Bethesda, MD (US); Boris Geller, Germantown, MD (US)

(73) Assignee: Fusion UV Systems, Inc., Gaithersburg, MD (US)

( * ) Notice: Subject to any disclaimer, the term of this patent is extended or adjusted under 35 U.S.C. 154(b) by 309 days.

This patent is subject to a terminal disclaimer.

(21) Appl. No.: 10/632,893

(22) Filed: Aug. 4, 2003

(65) Prior Publication Data

US 2004/0021090 A1 Feb. 5, 2004

Related U.S. Application Data

(63) Continuation-in-part of application No. 10/206,976, filed on Jul. 30, 2002, now Pat. No. 6,614,028.

(51) Int. Cl.
*G01N 23/12* (2006.01)
(52) U.S. Cl. ............... 250/432 R; 250/435; 250/492.1; 250/504 R
(58) Field of Classification Search ............. 250/432 R
See application file for complete search history.

(56) References Cited

U.S. PATENT DOCUMENTS

| | | | |
|---|---|---|---|
| 1,145,140 A | 7/1915 | Henri et al. | |
| 1,307,500 A | 6/1919 | Keyes | |
| 2,065,054 A | 12/1936 | Creighton et al. | |
| 3,801,773 A | 4/1974 | Matsumi | |
| 4,008,045 A | 2/1977 | Free | |
| 4,694,179 A * | 9/1987 | Lew et al. | 250/431 |
| 4,831,268 A | 5/1989 | Fisch et al. | |
| 5,034,235 A | 7/1991 | Dunn et al. | |
| 5,124,131 A | 6/1992 | Wekhof | |
| 5,136,491 A * | 8/1992 | Kano | 362/346 |
| 5,247,178 A | 9/1993 | Ury et al. | |
| 5,635,133 A | 6/1997 | Glazman | |
| 5,660,719 A | 8/1997 | Kurtz et al. | |

(Continued)

FOREIGN PATENT DOCUMENTS

FR          2 555 567          5/1985

(Continued)

*Primary Examiner*—Nikita Wells
*Assistant Examiner*—Phillip A. Johnston
(74) *Attorney, Agent, or Firm*—Finnegan, Henderson, Farabow, Garrett & Dunner, LLP

(57) ABSTRACT

Apparatus and a method for treating a fluid. The apparatus includes a fluid passageway, at least one source of irradiation, and curved reflecting troughs for reflecting irradiation onto the fluid passageway. A space is defined between the closed ends of the troughs. A first set of reflectors joins end edges of the trough open ends, and a second set of reflectors joins the top and bottom edges of the troughs and the first set of reflectors. The reflectors and troughs define a chamber. The fluid passageway and the at least one source of irradiation are positioned in the chamber, with each source of irradiation within a respective trough. At least one of the fluid passageway and the at least one source of irradiation is spaced from any focal axes so as to provide a substantially uniform irradiation distribution within the fluid in the fluid passageway.

78 Claims, 10 Drawing Sheets

U.S. PATENT DOCUMENTS

| | | |
|---|---|---|
| 5,973,331 A | 10/1999 | Stevens et al. |
| 5,989,283 A * | 11/1999 | Wilkens ...................... 607/88 |
| 6,013,917 A | 1/2000 | Ishiyama |
| 6,013,918 A | 1/2000 | Bushnell et al. |
| 6,083,387 A * | 7/2000 | LeBlanc et al. ............ 210/199 |
| 6,433,344 B1 | 8/2002 | Salisbury et al. |
| 6,590,217 B1 * | 7/2003 | Freeman et al. ............ 250/435 |
| 6,626,561 B2 * | 9/2003 | Carter et al. ................. 362/298 |
| 6,707,048 B2 * | 3/2004 | Hallett et al. ............... 250/431 |

FOREIGN PATENT DOCUMENTS

| | | |
|---|---|---|
| WO | 90/06899 | 6/1990 |
| WO | 96/33135 | 10/1996 |

* cited by examiner

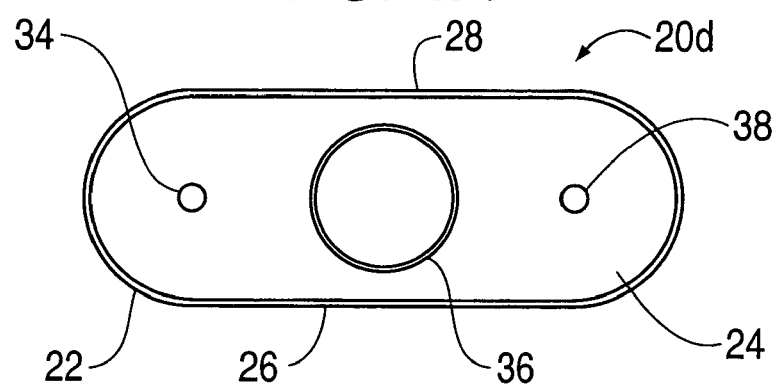
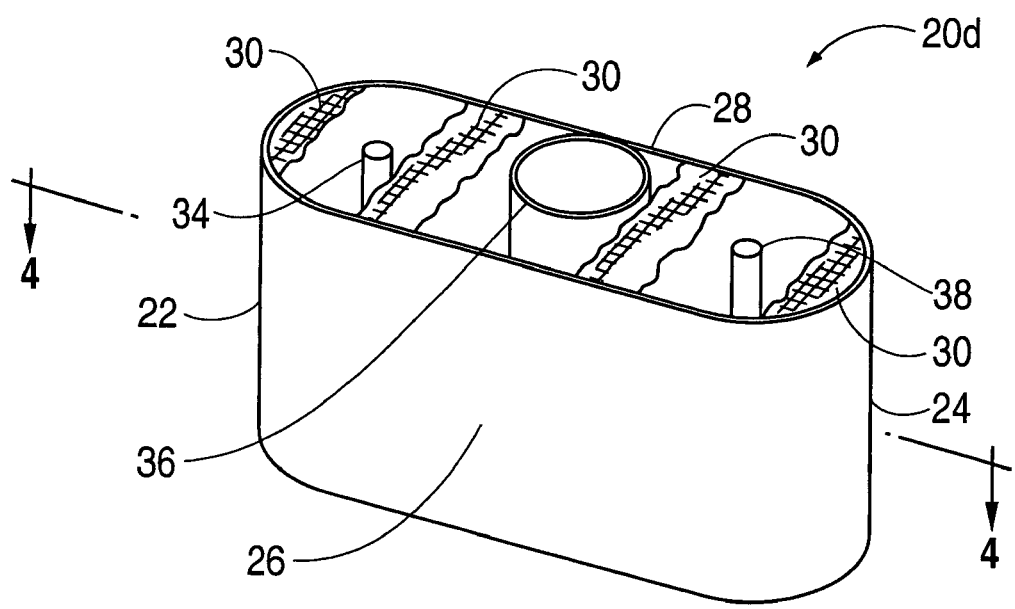

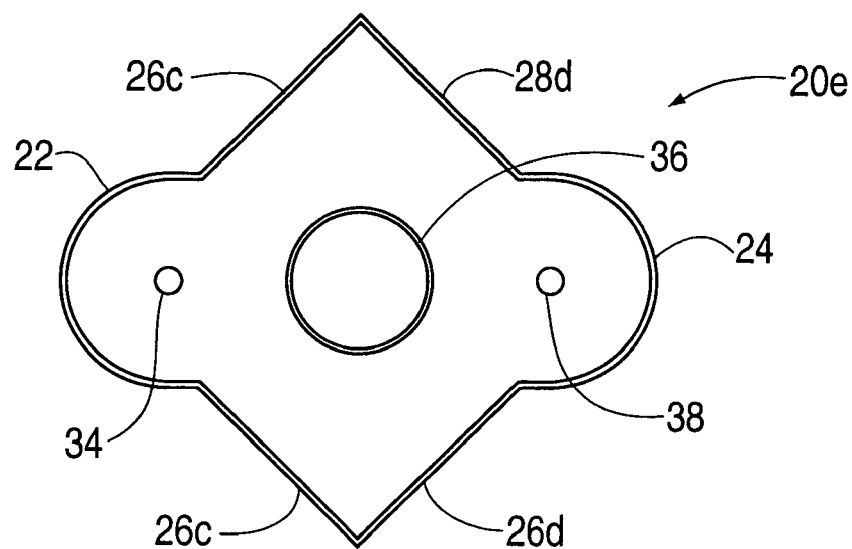
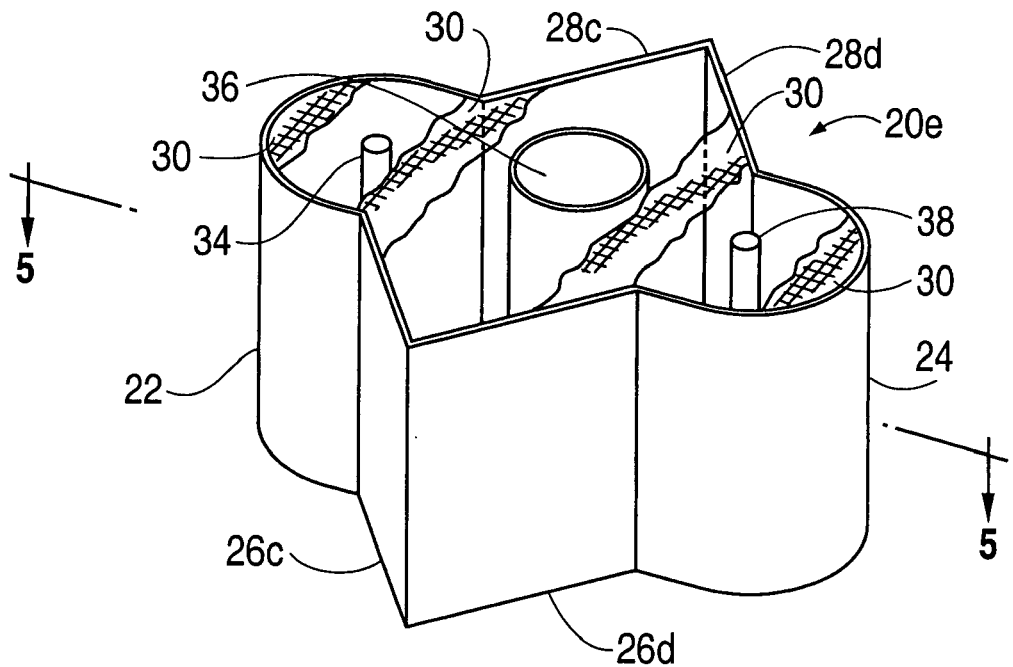

APPARATUS FOR AND METHOD OF TREATING A FLUID

CROSS REFERENCE TO RELATED APPLICATION

This application is a continuation-in-part of U.S. Pat. application Ser. No. 10/206,976 filed Jul. 30, 2002 now U.S. Pat. No. 6,614,028.

FIELD OF THE INVENTION

The present invention pertains to an apparatus for and a method of uniform treatment of fluid volumes using external irradiation sources. More particularly, the present invention pertains to an apparatus for and a method of treating a volume of fluid in a fluid passageway by irradiating the fluid passageway from an external irradiation source to provide a substantially uniform irradiation distribution within the fluid in the fluid passageway.

BACKGROUND OF THE INVENTION

During the irradiation treatment of fluids flowing through fluid passageways, the uniformity of irradiation is of primary importance. By way of example, the fluid might be treated with ultraviolet irradiation so as to disinfect, purify, or cause oxidation of material within the fluid. If the irradiation is not uniform, those portions of the fluid flowing through the regions of low irradiation intensity may be undertreated, while portions in the vicinity of peak irradiation fields may receive higher than desired doses of irradiation which could damage material within the fluid. This problem is even more significant in the case of turbid fluids or fluids of high absorptivity for the applied irradiation.

Known techniques for irradiation of volumes of fluid include immersing multiple irradiation sources in the fluid. However, this is complex and costly, requiring multiple irradiation sources and introducing additional problems of cumulative absorption caused by impurities on the irradiation source-fluid interface. Cleaning mechanisms and processes have been proposed to overcome this last problem, but these are likewise elaborate and complex. Potential irradiation source accidents introduce additional risks of pollution of the fluid and the distribution system by the hazardous irradiation source components.

A second approach is to restrict the fluid flow, avoiding underexposed volumes. This scheme suffers from limited efficiency, high pressure drops, and high cost of pumps necessary to achieve the desired flow.

Another approach is to introduce mixing devices in the fluid flow, in the hope that each portion of the fluid will receive an "average" treatment. This approach likewise suffers from efficiency problems, as well as the more serious problems of likely undertreatment of a portion of the fluid volume.

A further approach is to present the fluid as a thin film to the irradiation. This approach does not take into account the absorption of the source, the fluid passageway, and the fluid itself, nor the indices of refraction of the fluid passageway material or the fluid, and hence the real energy distribution in the thin film of fluid.

SUMMARY OF THE INVENTION

The present invention is an apparatus for and a method of uniformly treating fluid volumes. In accordance with the present invention a fluid passageway is provided, through which the fluid flows. At least one source of irradiation, external to the fluid passageway, produces irradiation to irradiate the fluid flowing within the fluid passageway. The apparatus further includes a plurality of curved troughs for reflecting light from the at least one source of irradiation onto the fluid flowing within the fluid passageway. Each trough has a curved cross section, with a closed end, top and bottom edges, and an open end with first and second end edges. The open end of the first trough faces the open end of the second trough to define a space between the closed ends of the troughs. The top edges of the first and second troughs define a first plane, while the bottom edges of the first and second troughs define a second plane. A first set of reflectors joins the end edges of the first trough to the end edges of the second trough. Each reflector of the first set of reflectors has a top edge lying substantially in the first plane and a bottom edge lying substantially in the second plane. A second set of reflectors joins the top edges of the troughs and the top edges of the first set of reflectors and joins the bottom edges of the troughs and the bottom edges of the first set of reflectors. The first and second sets of reflectors and the troughs cooperate to define a substantially closed chamber. The fluid passageway passes through the chamber, and each source of irradiation is positioned in the chamber. At least one of the fluid passageway and the at least one source of irradiation is spaced from any focal axis of the troughs so that the irradiation irradiating the fluid passageway is defocused. As a consequence, the fluid in the passageway is irradiated with a substantially uniform irradiation distribution, even in a fluid passageway of relatively large internal diameter.

BRIEF DESCRIPTION OF THE DRAWINGS

These and other aspects and advantages of the present invention are more apparent from the following detailed description and claims, particularly when considered in conjunction with the accompanying drawings. In the drawings:

FIGS. 4A and 4B are, respectively, a sectional view and a partially broken perspective view illustrating a fourth embodiment of an apparatus and a method in accordance with the present invention, with FIG. 4A taken along line 4-4 in FIG. 4B;

FIGS. 5A and 5B are, respectively, a sectional view and a partially broken perspective view illustrating a fifth embodiment of an apparatus and a method in accordance with the present invention, with FIG. 5A taken along line 5-5 in FIG. 5B;

DETAILED DESCRIPTION OF PREFERRED EMBODIMENTS

Figure 1A:
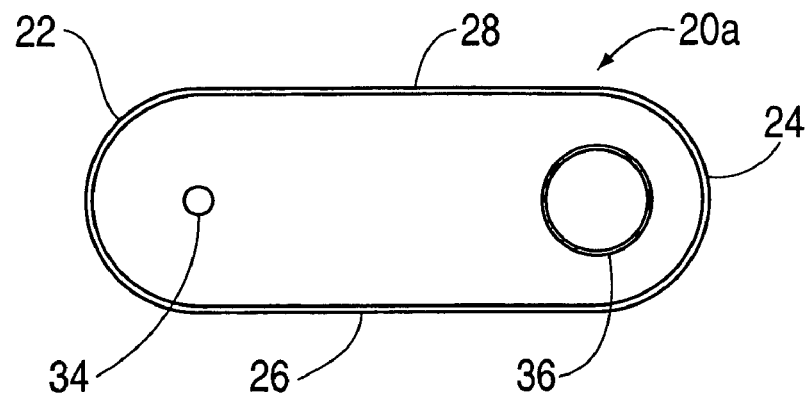
FIG. 1A is a sectional view, taken along line 1-1 in FIG. 1B, illustrating a first embodiment of an apparatus and a method in accordance with the present invention.
Figure 1B:
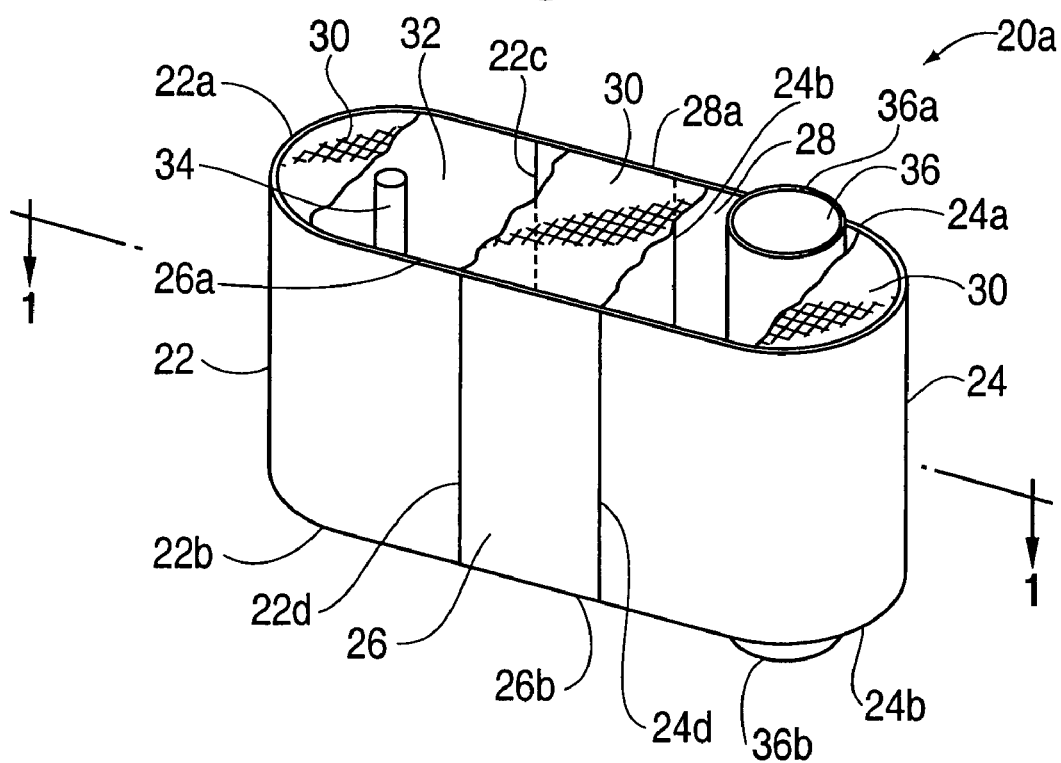
FIG. 1B is a perspective view, partially broken, of the apparatus of FIG. 1A.

FIGS. 1A and 1B depict a first embodiment of an apparatus 20a in accordance with the present invention. Apparatus 20a includes a first curved reflecting trough 22 and a second curved reflecting trough 24. The curve of each trough might be any second order curve, such as a parabola or an ellipse, or might be a combination of a parabolic closed end an elliptical sides. Likewise, each curve could be defined by a plurality of segments of second order curves or by a set of coordinates or in any other way. All that is required is that each trough reflect irradiation from a point within its curve toward the other trough. The curve may have one or more focal points, as in a second order curve, but that is not essential. Likewise, the curve may have a major axis and possibly a minor axis.

Each trough 22, 24 has a closed end, top and bottom edges 22a, 22b, 24a, 24b, and an open end. The top edges 22a, 24a define a plane, and the bottom edges 22b, 24b define a plane. The open end of each trough 22, 24 has two end edges 22c, 22d, 24c, 24d. The open ends of troughs 22 and 24 face each other to define a space having a longitudinal axis, which may be a major axis of a second order curve. End edges 22c, 22d of trough 22 are connected to the end edges 24c, 24d, respectively, of trough 24 by continuous flat reflectors 26, 28. Each flat reflector 26, 28 has a top edge 26a, 28a and a bottom edge 26b, 28b. Top edges 26a, 28a lie in the plane defined by top edges 22a, 24a, and bottom edges 26b, 28b lie in the plane defined by bottom edges 22b, 24b.

A flat reflector 30 joins the top edges 22a, 26a, 28a, 24a of trough 22, flat reflectors 26, 28, and trough 24. Another flat reflector (not shown) joins the bottom edges 22b, 26b, 28b, 24b of trough 22, flat reflectors 26, 28 and trough 24 and cooperates with troughs 22, 24 and flat reflectors 26, 28 and 30 to define a chamber 32.

A source of irradiation 34 is positioned within trough 22, and so within chamber 32. Irradiation source 34 might be a light source such as a source of ultraviolet light. By way of example, irradiation source 34 might be a microwave electrodeless discharge bulb, such as a tubular bulb, or might be an arc discharge bulb or a fluorescent discharge bulb. A fluid passageway 36 pass through chamber 32. Preferably, when irradiation source 34 is an elongated tube, fluid passageway 36 has a longitudinal axis that is parallel to the longitudinal axis of source 34. Fluid passageway 36 has an inlet end 36a, which is adapted to be connected to a source of fluid to be treated, and an outlet end 36b, which is adapted to be connected to a destination for the fluid after treatment.

If trough 22 or trough 24, or both, have a focal axis, then either irradiation source 34 or fluid passageway 36, or both, is spaced from all such focal axes. If desired, an adjustable mount can be provided making the position of irradiation source 34 or of fluid passageway 36, or both, adjustable. The mount might be adjustable on trough 22 or 24 or another mounting surface, or irradiation source 34 or fluid passageway 36 might be adjustable on the mount. As a consequence, the irradiation from source 34 is not focused on fluid passageway 36. Therefore, irradiation from source 34 irradiates the fluid within fluid passageway 36 with a substantially uniform irradiation distribution. The irradiation has a substantially two-dimensionally uniform irradiation distribution across the cross-section of fluid passageway 36, as well as a substantially three-dimensional uniform irradiation distribution within the volume of fluid in the fluid passageway.

Figure 2A:
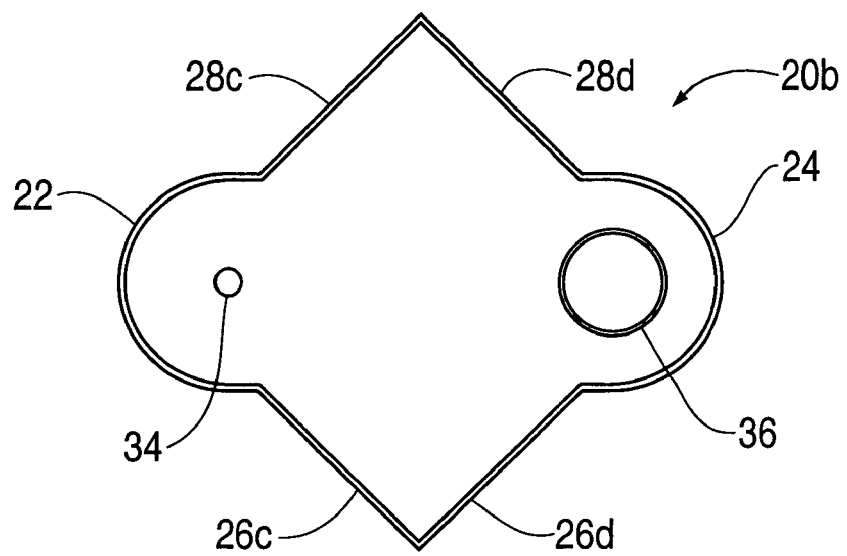
FIGS. 2A and 2B are, respectively, a sectional view and a partially broken perspective view illustrating a second embodiment of an apparatus and a method in accordance with the present invention, with FIG. 2A taken along line 2-2 in FIG. 2B.
Figure 2B:
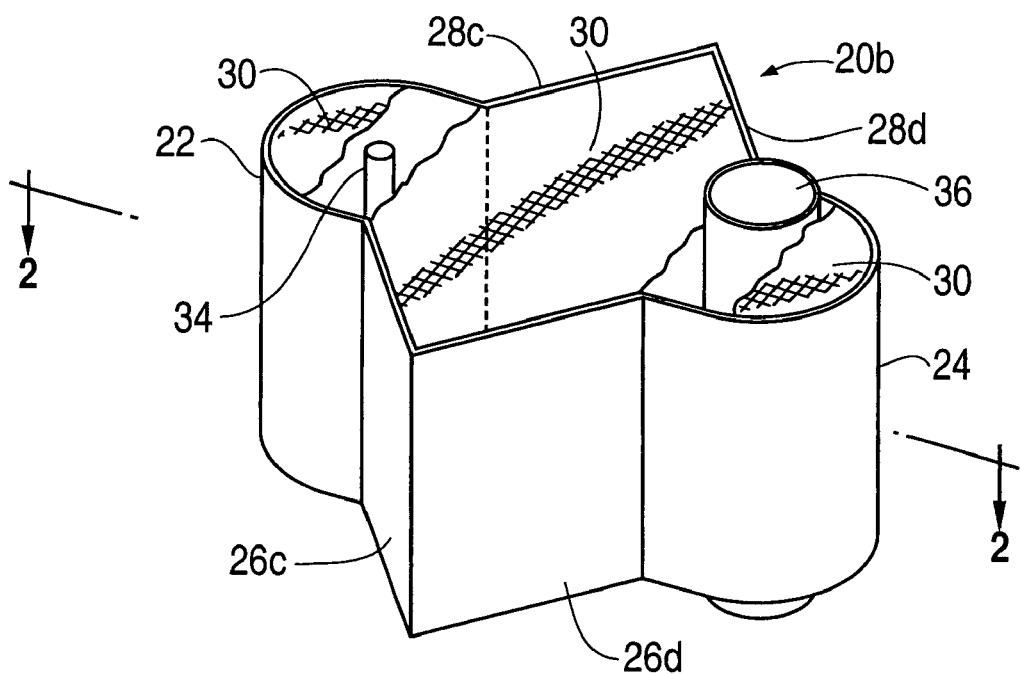

FIGS. 2A and 2B depict a second embodiment of an apparatus 20b in accordance with the present invention. Apparatus 20b differs from apparatus 20a of FIGS. 1A-1B in that continuous flat reflectors 26 and 28 have been replaced by segmented flat reflectors 26c, 26d and segmented flat reflectors 28 and 28d, respectively, which are angled with respect to the longitudinal axis of apparatus 20b. Consequently, flat reflectors 26c and 26d meet at a V, as do flat reflectors 28c and 28d. Again, the irradiation from source 34 is defocused as it reaches fluid passageway 36, and so the irradiation has a substantially uniform distribution within the fluid in the passageway. The angled flat reflectors reflect the irradiation in a manner resulting in more uniform irradiance on the areas of fluid passageway 36 which are remote from irradiation source 34 by being ±90° or more from the longitudinal axis of the space within chamber 32, including areas on the side of fluid passageway 36 opposite irradiation source 34.

Figure 3A:
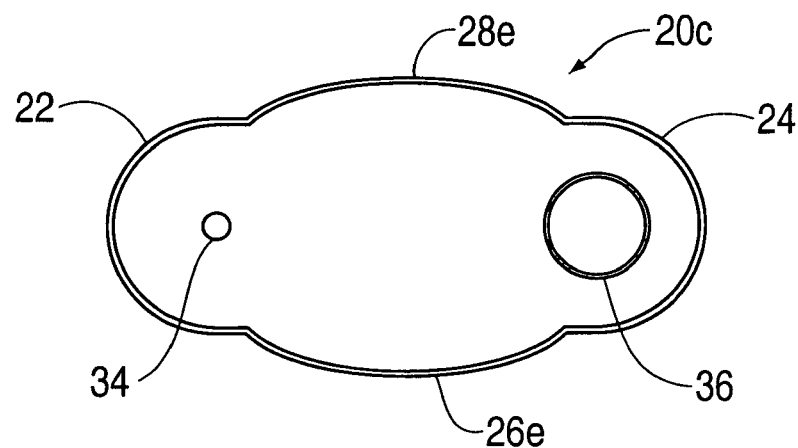
FIGS. 3A and 3B are, respectively, a sectional view and a partially broken perspective view illustrating a third embodiment of an apparatus and a method in accordance with the present invention, with FIG. 3A taken along line 3-3 in FIG. 3B.
Figure 3B:
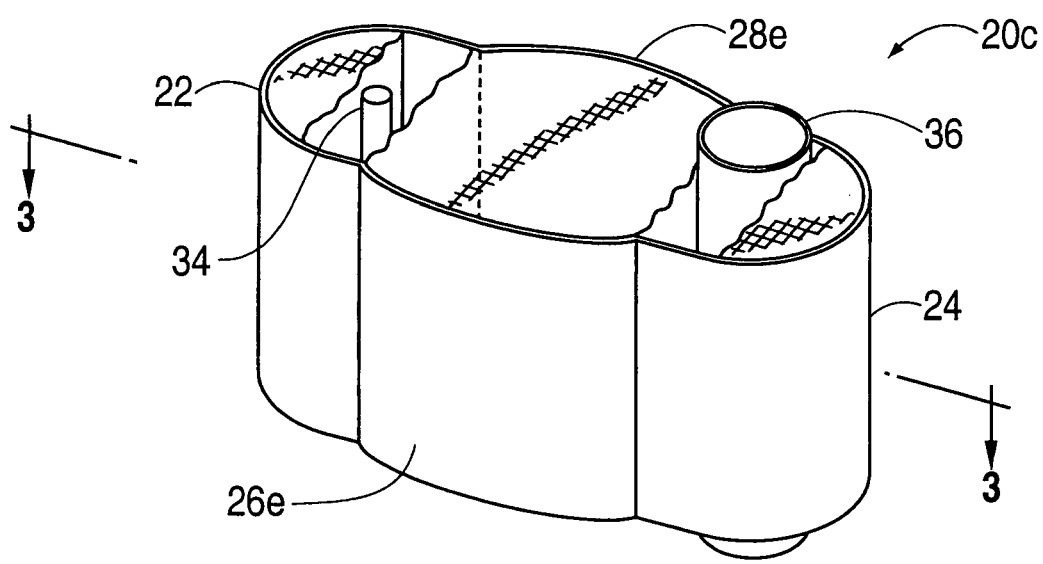

FIGS. 3A and 3B depict a third embodiment of an apparatus 20c in accordance with the present invention. Apparatus 20c differs from apparatus 20a of FIGS. 1A-1B in that continuous flat reflectors 26 and 28 are replaced by curved reflectors 26e and 28e. Again, the curved reflectors 26e, 28e improve the uniformity of the radiation level on the area of fluid passageway remote from irradiation source 34.

FIGS. 4A and 4B depict a fourth embodiment of an apparatus 20d in accordance with the present invention. Apparatus 20d differs from apparatus 20a of FIGS. 1A-1B in that the troughs 22, 24 of apparatus 20d are spaced further apart along the longitudinal axis of apparatus 20d. For example, if troughs 22 and 24 are elliptical, each trough has a first focal axis within the trough and a second focal axis beyond the trough, and the second focal axes coincide. Continuous flat reflectors 26, 28 and 30, and a flat reflector joining the bottom edges of troughs 22 and 24 and reflectors 26 and 28 are provided, as in the apparatus 20a of FIG. 1. Apparatus 20d has a first irradiation sources 34 which is at or adjacent the first focal point of trough 22 and a second irradiation source 38 which is at or adjacent the first focal point of trough 24. Fluid passageway 36 is at or adjacent the coincident second focal axes. Either the two irradiation sources 34, 38 are spaced from the first focal axes, or fluid passageway 36 is spaced from the second focal axes, or both. Because of this spacing, the irradiation from sources 34, 36 is defocused as it reaches fluid passageway 36, and so the irradiation has a substantially uniform distribution within the fluid in the passageway.

FIGS. 5A and 5B depict a fifth embodiment of an apparatus 20e in accordance with the present invention. Apparatus 20e differs from apparatus 20b of FIGS. 2A and 2B by having two irradiation sources 34, 38, in the same manner as apparatus 20d of FIGS. 4A-4B.

Figure 6A:
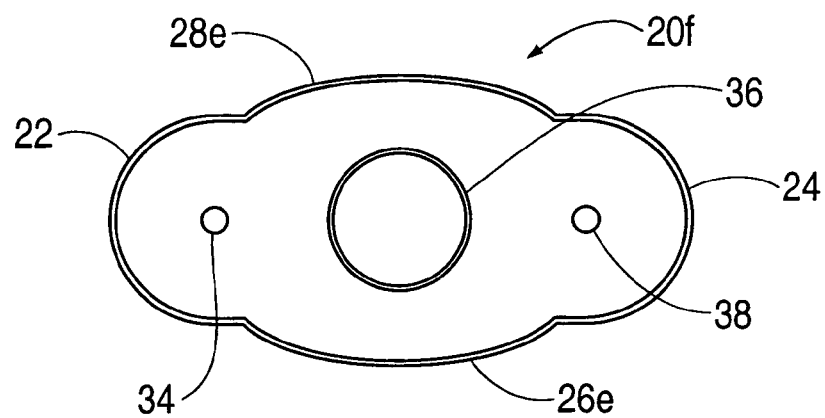
FIGS. 6A and 6B are, respectively, a sectional view and a partially broken perspective view illustrating a sixth embodiment of an apparatus and a method in accordance with the present invention, with FIG. 6A taken along line 6-6 in FIG. 6B.
Figure 6B:
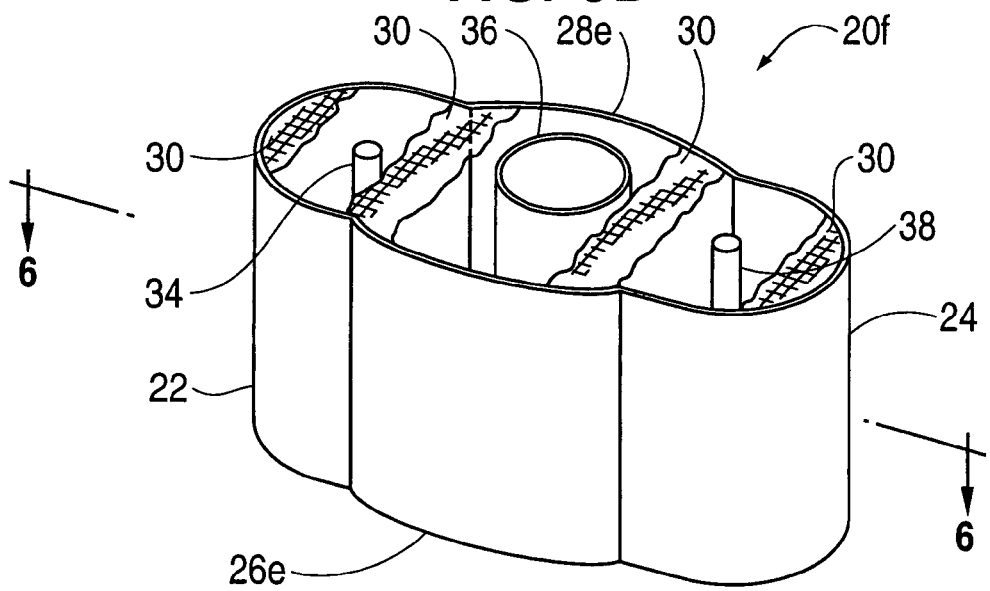

FIGS. 6A and 6B depict a sixth embodiment of an apparatus 20f in accordance with the present invention. Apparatus 20f differs from apparatus 20c of FIGS. 3A-3B by having two irradiation sources 34, 38, in the same manner as apparatus 20d of FIGS. 4A-4B.

Figure 7:
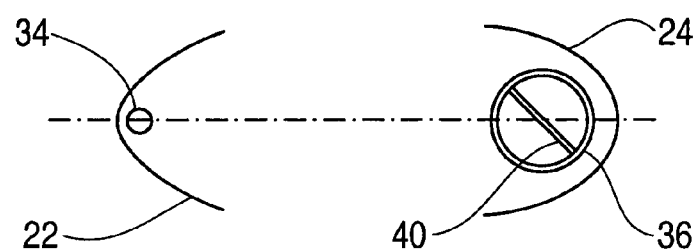
FIG. 7 illustrates a detection plane useful in determining irradiance patterns in an apparatus and method in accordance with the present invention.
Figure 8A:
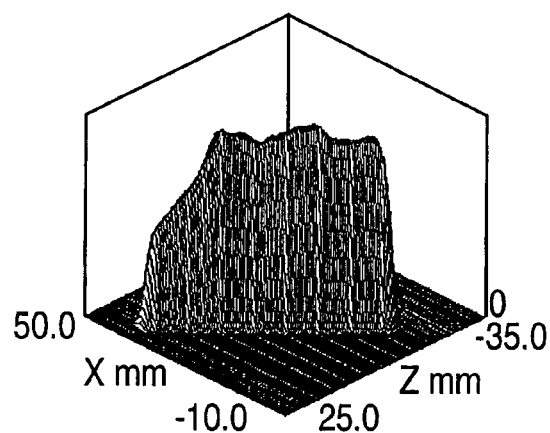
FIGS. 8A-8H illustrate irradiance patterns on different detection planes in various apparatuses in accordance with the present invention.

FIG. 7 illustrates a 45° detection plane 40 on which the irradiation within fluid passageway 36 is measured. FIGS. 8A-8H illustrate irradiation patterns on detection places at various angles within fluid passageway 36 in various of apparatuses in accordance with the present invention. These figures were obtained from computer simulations of the various apparatuses. FIG. 8A illustrates the 45° irradiation pattern in an apparatus 20a of FIGS. 1A-1B having an elliptical reflector 22 and a parabolic reflector 24 and having a fluid passageway 36 with an internal diameter of 50 mm. As can be seen, the irradiation is substantially uniform over the width of the fluid passageway, resulting in a substantially uniform irradiation distribution within the fluid in fluid passageway 36.

Figure 8B:
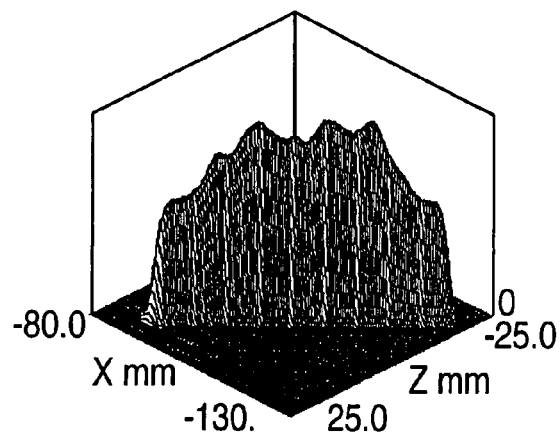
Figure 8C:
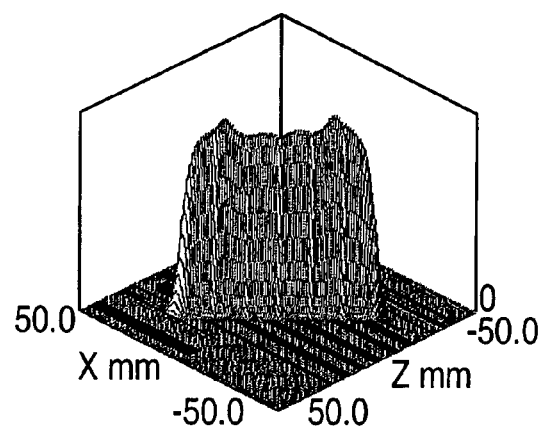
Figure 8D:
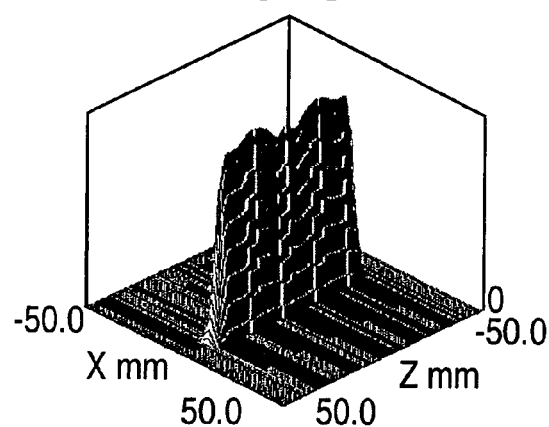
Figure 8E:
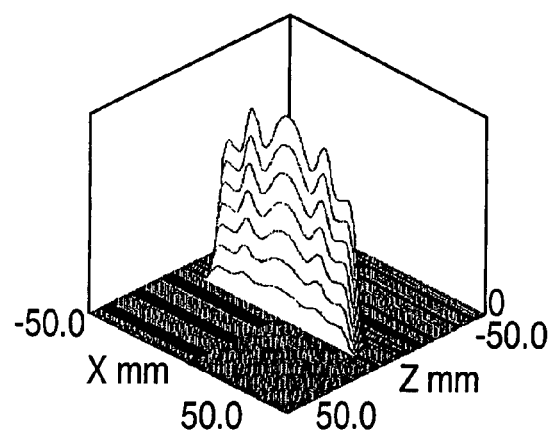
Figure 8F:
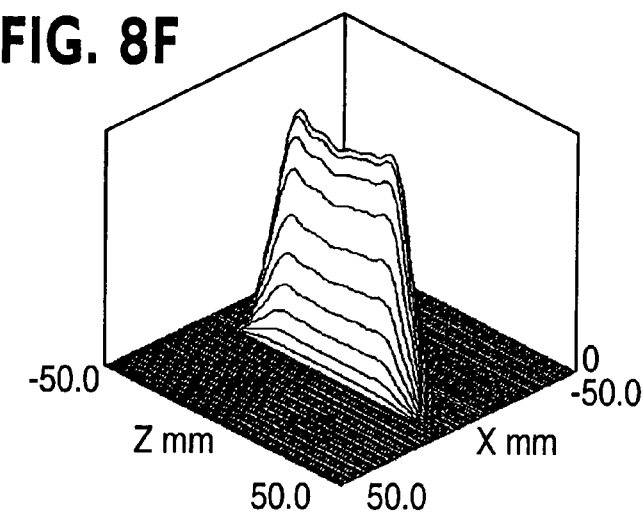
Figure 8G:
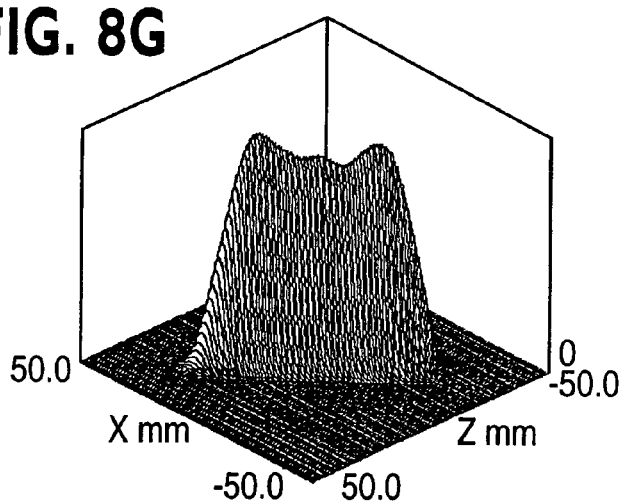
Figure 8H:
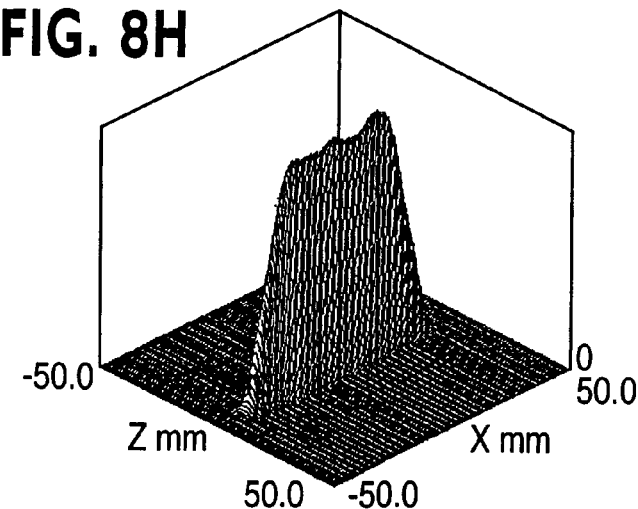

FIG. 8B illustrates the 45° irradiation pattern in an apparatus 20b of FIGS. 2A-2B having elliptical reflectors 22 and 24 and a fluid passageway 36 with an internal diameter of 50 mm. Again, the irradiation distribution is substantially uniform.

FIG. 7C illustrates the 45° irradiation pattern in an apparatus 20d of FIGS. 4A-4B. The irradiation distribution is substantially uniform within the fluid in fluid passageway 36.

FIG. 7D illustrates the 90° irradiation pattern in an apparatus 20d of FIGS. 4A-4B. The irradiation distribution is substantially uniform within the fluid passageway 36.

FIG. 7E illustrates the 0° irradiation pattern in an apparatus 20d of FIGS. 4A-4B. Still, the irradiation distribution is substantially uniform within the fluid in fluid passageway 36.

FIG. 7F illustrates the 0° irradiation pattern in an apparatus 20e of FIGS. 5A-5B with elliptical reflectors 22 and 24 and a fluid passageway 36 having an internal diameter of 70 mm. The irradiation distribution is again substantially uniform within the fluid in fluid passageway 36.

FIG. 7G illustrates the 450 irradiation pattern in an apparatus 20e of FIGS. 5A-5B with elliptical reflectors 22 and 24 and a fluid passageway 36 having an internal diameter of 70 mm. The irradiation distribution is substantially uniform within the fluid in fluid passageway 36.

FIG. 7H illustrates the 90° irradiation pattern in an apparatus 20e of FIGS. 5A-5B with elliptical reflectors 22 and 24 and a fluid passageway 36 having an internal diameter of 70 mm. Once again, the irradiation distribution is substantially uniform within the fluid in fluid passageway 36.

Figure 9:
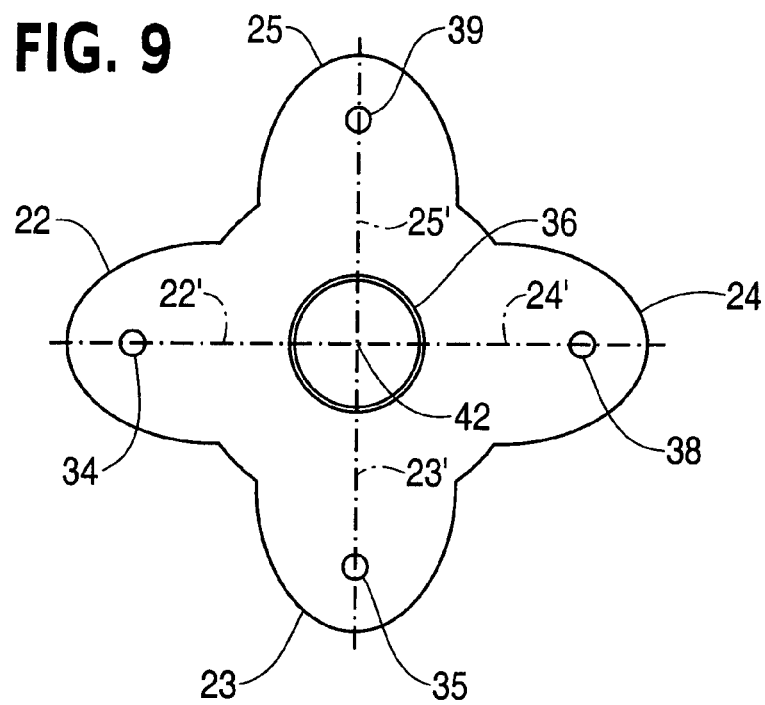
FIGS. 9 and 10 are sectional views illustrating further embodiments of an apparatus and method in accordance with the present invention.

While apparatuses with two reflecting troughs have been illustrated and described above, any number N of troughs could be provided, with the longitudinal axis of each trough intersecting the longitudinal axis of its angularly adjacent troughs at an angle $2\pi/N$, where N is the number of troughs. By way of example, FIG. 9 illustrates an apparatus having four reflecting troughs 22, 23, 24, 25 and four irradiation sources 34, 35, 38, 39. Each reflecting trough has a longitudinal axis 22', 23', 24', 25'. Each radiation source 34, 35, 38, 39 is at or adjacent the longitudinal axis 22', 23', 24'25' of its respective trough. Longitudinal axes 22' and 24' coincide, and longitudinal axes 23' and 25' coincide. The longitudinal axes intersect at a single intersection 42. Fluid passageway 36 is centered at or adjacent intersection 42. Either each irradiation source 34, 35, 38, 39 is spaced from its respective longitudinal axis 22', 23', 24', 25', or fluid passageway is centered slightly spaced from intersection 42, or both. As a result, the irradiation irradiates the fluid within passageway 36 with a substantially uniform distribution.

Figure 10:
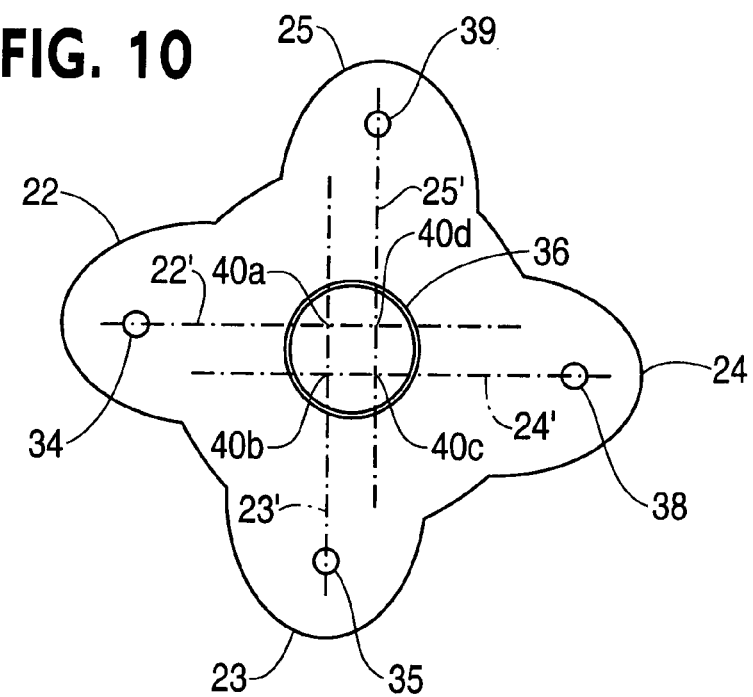

As a further example, FIG. 10 illustrates an apparatus also having four reflecting troughs 22, 23, 24, 25 with longitudinal axes 22', 23', 24', 25'. However, axes 22' and 24' do not coincide, although preferably they are offset in a direction substantially perpendicular to their longitudinal axes and so are parallel, and axes 23' and 25' do not coincide, but preferably also are offset in a direction substantially perpendicular to their longitudinal axes, and so are parallel. The longitudinal axes intersect within fluid passageway 36 at intersection 40a, 40b, 40c, 40d. Preferably, intersections 40a, 40b, 40c, 40d define a figure having a center of symmetry. Preferably, also, fluid passageway 36 has a longitudinal axis which passes through that center of symmetry. The irradiation is not focused within fluid passageway 36, and so a substantially uniform radiation distribution is obtained.

The present invention thus provides an improved apparatus for and method of treatment of fluids. Fluid can be treated by passing it through the fluid passageway of an apparatus in accordance with the present invention and irradiating the fluid with a substantially uniform irradiation distribution. Although the invention has been described with reference to preferred embodiments, various alterations, rearrangements, and substitutions might be made, and still the result would be within the scope of the invention.

What is claimed is:

1. Apparatus for treating a volume of fluid, said apparatus comprising: a fluid passageway through which the fluid flows; at least one source of irradiation, external to said fluid passageway; at least two reflecting troughs, each trough having a curved cross section, with a closed end, top and bottom edges, and an open end, the open end of each trough having first and second end edges, the open end of said first trough facing the open end of said second trough to define a space between the closed ends of said troughs, the top edges of said first and second troughs defining a first plane, and the bottom edges of said first and second troughs defining a second plane; a first set of reflectors joining the end edges of said first trough to the end edges of said second trough, each reflector of said first set of reflectors having a top edge lying substantially in the first plane and a bottom edge lying substantially in the second plane; and a second set of reflectors joining the top edges of said troughs and of said first set of reflectors and joining the bottom edges of said troughs and of said first set of reflectors, said second set of reflectors cooperating with said troughs and said first set of reflectors to define a substantially enclosed chamber having said at least one source of irradiation therein and having said fluid passageway passing therethrough, wherein: each source of irradiation is within a respective one of said troughs, and at least one of said fluid passageway and said at least one source of irradiation is spaced from all focal axes of said troughs so as to provide a substantially uniform irradiation distribution within the fluid in said fluid passageway, wherein each trough has a longitudinal axis, and wherein each reflector of said first set of reflectors is segmented and comprises: a first flat reflector segment extending from a first one of said troughs at an angle to the longitudinal axis of such trough; and a second flat reflector segment extending from a second one of said troughs at an angle to the longitudinal axis of that trough and cooperating with said first flat reflector segment to define a V substantially midway between said troughs.

2. Apparatus according to claim 1, wherein at least one of said troughs has a cross section defined by a plurality of segments of second order curves.

3. Apparatus according to claim 1, wherein at least one of said troughs has a cross section defined by a set of coordinates.

4. Apparatus according to claim 1, wherein at least one of said troughs has a cross section defined by a second order curve.

5. Apparatus according to claim 4, wherein the second order curve is a parabola.

6. Apparatus according to claim 4, wherein the second order curve is a portion of an ellipse.

7. Apparatus as claimed in claim 1, wherein each reflector of said first set of reflectors is a continuous reflector.

8. Apparatus according to claim 1, wherein the V forms an angle of substantially 90°.

9. Apparatus according to claim 1, wherein each reflector of said first set of reflectors is curved.

10. Apparatus according to claim 1, wherein each source of irradiation comprises a source of light for producing light to irradiate said fluid passageway.

11. Apparatus according to claim 10, wherein each source of light comprises a source of ultraviolet light.

12. Apparatus according to claim 11, wherein each source of ultraviolet light comprises a microwave electrodeless discharge bulb.

13. Apparatus according to claim 11, wherein each source of ultraviolet light comprises an arc discharge bulb.

14. Apparatus according to claim 11, wherein each source of ultraviolet light comprises a fluorescent discharge bulb.

15. Apparatus according to claim 10, wherein said fluid passageway has a central axis, and each source of light comprises a tubular bulb having a longitudinal axis substantially parallel to the central axis of said fluid passageway.

16. Apparatus according to claim 1, wherein said fluid passageway has a central axis, and each source of irradiation has a tubular shape with a longitudinal axis substantially parallel to the central axis of said fluid passageway.

17. Apparatus according to claim 1, wherein both said at least one source of irradiation and said fluid passageway are spaced from all focal axes of said troughs.

18. Apparatus according to claim 9, wherein each trough has a longitudinal axis, and said fluid passageway is on one of the longitudinal axes.

19. Apparatus according to claim 1, wherein each trough has a longitudinal axis, and said fluid passageway is spaced from all the longitudinal axes.

20. Apparatus according to claim 1, wherein said fluid passageway and said at least one source of irradiation are positioned so as to provide a substantially two-dimensionally uniform irradiation distribution across a cross-sectional plane of the fluid flowing in said fluid passageway.

21. Apparatus according to claim 1, wherein said fluid passageway and said at least one source of irradiation are positioned so as to provide a substantially three-dimensionally uniform irradiation distribution within a volume of fluid flowing in said fluid passageway.

22. Apparatus according to claim 1, wherein each trough has a focal axis within the trough, and each source of irradiation is positioned between the focal axis and the elliptical end of the respective one of said troughs.

23. Apparatus according to claim 1, wherein each trough has a first focal axis and a second focal axis, and the second focal axes of all of said troughs are substantially coincident.

24. Apparatus according to claim 1, wherein each trough has a longitudinal axis, and the longitudinal axes define a figure having a center of symmetry.

25. Apparatus as claimed in claim 24, wherein said source of irradiation has a longitudinal axis, and said fluid passageway has a central axis extending substantially through the center of symmetry of the figure and substantially parallel to the longitudinal axis of said source of irradiation.

26. Apparatus as claimed in claim 1, having a single source of irradiation and two troughs.

27. Apparatus as claimed in claim 26, wherein each trough has a focal axis, and said fluid passageway is on the focal axis of one of said troughs, and said source of irradiation is spaced from the focal axes and is adjacent the focal axis of the other said troughs.

28. Apparatus as claimed in claim 26, wherein each trough has a focal axis, and said source of irradiation is on the focal axis of one of said troughs, and said fluid passageway is spaced from the focal axes and is adjacent the focal axis of the other of said troughs.

29. Apparatus according to claim 26, wherein said two troughs have coinciding longitudinal axes.

30. Apparatus as claimed in claim 26, wherein said two troughs have non-coinciding longitudinal axes.

31. Apparatus as claimed in claim 30, wherein said two troughs have parallel longitudinal axes.

32. Apparatus as claimed in claim 31, wherein said source of irradiation has a longitudinal axis, and said fluid passageway has a central axis extending between the longitudinal axes of said troughs and substantially parallel to the longitudinal axis of said source of irradiation.

33. Apparatus according to claim 30, wherein said source of irradiation is on the longitudinal axis of one of said troughs and said fluid passageway is on the longitudinal axis of the other of said troughs.

34. Apparatus as claimed in claim 1, having two sources of irradiation and two troughs.

35. Apparatus as claimed in claim 34, wherein each trough has a first focal axis and a second focal axis, the second focal axes of said troughs coincide, said fluid passageway is on the second focal axes, and each of said sources of irradiation is spaced from a respective one of the first focal axes.

36. Apparatus as claimed in claim 34, wherein each trough has a first focal axis and a second focal axis, the second focal axes of said troughs coincide, each of said two sources of irradiation is on the first focal axis of a respective one of said troughs, and said fluid passageway is spaced from the second focal axes.

37. Apparatus according to claim 34, wherein said two troughs have coinciding longitudinal axes.

38. Apparatus as claimed in claim 34, wherein said two troughs have non-coinciding longitudinal axes.

39. Apparatus as claimed in claim 38, wherein said two troughs have parallel longitudinal axes.

40. Apparatus as claimed in claim 39, wherein said sources of irradiation have parallel longitudinal axes, and said fluid passageway has a central axis extending between the longitudinal axes of said troughs and substantially parallel to the longitudinal axes of said sources of irradiation.

41. Apparatus according to claim 38, wherein said source of irradiation is on the longitudinal axis of one of said troughs and said fluid passageway is on the longitudinal axis of the other of said troughs.

42. Apparatus according to claim 1, wherein each trough has a longitudinal axis, and the longitudinal axis of each trough intersects the longitudinal axis of each angularly adjacent trough at an angle equal to $2\pi/N$, where N is the number of troughs.

43. Apparatus according to claim 42, wherein the longitudinal axes of the troughs intersect at a single intersection.

44. Apparatus according to claim 43, wherein said fluid passageway has a central axis passing through the intersection of the longitudinal axes.

45. Apparatus according to claim 42, wherein said fluid passageway has a central axis passing through the center of symmetry of a figure defined by the points of intersection of the longitudinal axes of said troughs.

46. Apparatus according to claim 42, having four sources of irradiation, and wherein N=4.

47. Apparatus as claimed in claim 46, wherein the longitudinal axes of said troughs intersect at a single intersection.

48. Apparatus according to claim 47, wherein said fluid passageway has a central axis passing through the intersection of the longitudinal axes.

49. Apparatus according to claim 46, wherein said fluid passageway has a central axis passing through the center of symmetry of a figure defined by the points of intersection of the longitudinal axes of said troughs.

50. Apparatus according to claim 1, further comprising a mount for each source of irradiation, making the position of each source of irradiation adjustable so as to provide a substantially two-dimensionally uniform irradiation distribution within fluid flowing in said fluid passageway.

51. Apparatus as claimed in claim 50, wherein each mount is adapted to be adjustably positioned on a mounting surface.

52. Apparatus as claimed in claim 50, wherein each source of irradiation is adjustably mounted to said mount.

53. Apparatus according to claim 1, further comprising a mount for each source of irradiation, making the position of each source of irradiation adjustable so as to provide a substantially three-dimensionally uniform irradiation distribution within fluid flowing in said fluid passageway.

54. Apparatus as claimed in claim 53, wherein each mount is adapted to be adjustably positioned on a mounting surface.

55. Apparatus as claimed in claim 53, wherein each source of irradiation is adjustably mounted to said mount.

56. Apparatus according to claim 1, further comprising a mount for each trough, making the position of each trough adjustable so as to provide a substantially two-dimensionally uniform irradiation distribution within fluid flowing in said fluid passageway.

57. Apparatus as claimed in claim 56, wherein each mount is adapted to be adjustably positioned on a mounting surface.

58. Apparatus as claimed in claim 56, wherein each trough is adjustably mounted to one of said mounts.

59. Apparatus according to claim 1, further comprising a mount for each trough, making the position of each trough adjustable so as to provide a substantially three-dimensionally uniform irradiation distribution within fluid flowing in said fluid passageway.

60. Apparatus as claimed in claim 59, wherein each mount is adapted to be adjustably positioned on a mounting surface.

61. Apparatus as claimed in claim 59, wherein each trough is adjustably mounted to one of said mounts.

62. Apparatus according to claim 1, further comprising an adjustable mount for said fluid passageway, making the position of said fluid passageway adjustable so as to provide a substantially two-dimensionally uniform irradiation distribution within fluid flowing in said fluid passageway.

63. Apparatus as claimed in claim 62, wherein said mount is adapted to be adjustably positioned on a mounting surface.

64. Apparatus as claimed in claim 62, wherein said fluid passageway is adjustably mounted to said mount.

65. Apparatus according to claim 1, further comprising an adjustable mount for said fluid passageway, making the position of said fluid passageway adjustable so as to provide a substantially three-dimensionally uniform irradiation distribution within fluid flowing in said fluid passageway.

66. Apparatus as claimed in claim 65, wherein said mount is adapted to be adjustably positioned on a mounting surface.

67. Apparatus as claimed in claim 65, wherein said fluid passageway is adjustably mounted to said mount.

68. A method of providing a substantially two-dimensionally uniform irradiation distribution across a cross-sectional plane of a fluid flowing in a fluid passageway, said method comprising:

providing the apparatus according to claim 1;

positioning at least one of (a) said fluid passageway and (b) said at least one source of irradiation such that defocused irradiation from said at least one source of irradiation irradiates the fluid in said fluid passageway with a substantially two-dimensionally uniform irradiation distribution; and activating said at least one source of irradiation.

69. A method of providing a substantially three-dimensionally uniform irradiation distribution within a volume of a fluid flowing in a fluid passageway, said method comprising:

providing the apparatus according to claim 1;

positioning at least one of (a) said fluid passageway and (b) said at least one source of irradiation such that defocused irradiation from said at least one source of irradiation irradiates the fluid in said fluid passageway with a substantially three-dimensionally uniform irradiation distribution; and activating said at least one source of irradiation.

70. A method of providing a substantially two-dimensionally uniform irradiation distribution across a cross-sectional plane of a fluid flowing in a fluid passageway, said method comprising:

providing the apparatus according to claim 1;

shifting at least one trough such that defocused irradiation from said at least one source of irradiation irradiates the fluid in said fluid passageway with a substantially two-dimensionally uniform irradiation distribution; and activating said at least one source of irradiation.

71. A method as claimed in claim 70, wherein said at least one trough has a longitudinal axis and is shifted in a direction substantially perpendicular to the longitudinal axis of such trough.

72. A method of providing a substantially uniform three-dimensional irradiation distribution within a volume of fluid flowing in a fluid passageway, said method comprising:

providing the apparatus according to claim 1;

shifting at least one trough such that defocused irradiation from said at least one source of irradiation irradiates the fluid in said fluid passageway with a substantially three-dimensionally uniform irradiation distribution; and activating said at least one source of irradiation.

73. A method as claimed in claim 72, wherein said at least one trough has a longitudinal axis and is shifted in a direction substantially perpendicular to the longitudinal axis of such trough.

74. A method of treating a fluid flowing in a fluid passageway, comprising:

providing the apparatus according to claim 1;

passing a fluid through said fluid passageway;

irradiating the fluid in said fluid passageway with irradiation produced by said at least one source of irradiation; and activating said at least one source of irradiation.

75. A method according to claim 74, wherein irradiating the fluid comprises irradiating the fluid with ultraviolet light.

76. A method according to claim 75, wherein said fluid includes a material to be disinfected, and wherein irradiating the fluid disinfects the material flowing in said fluid passageway.

77. A method according to claim 75, wherein the fluid includes a material to be purified, and wherein irradiating the fluid purifies the material flowing in said fluid passageway.

78. A method according to claim 75, wherein the fluid includes a material to be oxidized, and wherein irradiating the fluid causes oxidation of the material flowing in said fluid passageway.

* * * * *